(12) United States Patent
Addison

(10) Patent No.: US 6,509,388 B1
(45) Date of Patent: Jan. 21, 2003

(54) POLYURETHANE FOAMS FOR USE IN WOUND DRESSINGS

(75) Inventor: Deborah Addison, Lancaster (GB)

(73) Assignee: Johnson and Johnson Medical Limited, Edinburgh (GB)

( * ) Notice: Subject to any disclaimer, the term of this patent is extended or adjusted under 35 U.S.C. 154(b) by 0 days.

(21) Appl. No.: 09/913,181

(22) PCT Filed: Feb. 10, 2000

(86) PCT No.: PCT/GB00/00418

§ 371 (c)(1),
(2), (4) Date: Nov. 15, 2001

(87) PCT Pub. No.: WO00/47241

PCT Pub. Date: Aug. 17, 2000

(30) Foreign Application Priority Data

Feb. 11, 1999 (GB) .............................................. 9903097

(51) Int. Cl.⁷ .................................................. C08J 9/08
(52) U.S. Cl. ............................ 521/159; 521/67; 521/99; 521/102; 521/130; 521/137; 521/170; 521/174
(58) Field of Search ............................ 521/67, 99, 102, 521/137, 159, 170, 174, 130

(56) References Cited

U.S. PATENT DOCUMENTS

| 3,903,232 A | 9/1975 | Wood et al. ................. 264/157 |
| 4,339,550 A | 7/1982 | Palinczar et al. .............. 521/99 |
| 5,124,369 A * | 6/1992 | Vandichel et al. ........... 521/125 |
| 5,629,014 A * | 5/1997 | Kwiatek et al. ............. 424/448 |
| 5,844,013 A * | 12/1998 | Kenndoff et al. ............. 156/78 |
| 5,914,125 A * | 6/1999 | Andrews et al. ............. 424/443 |
| 6,326,410 B1 * | 12/2001 | Cheong ...................... 521/117 |

FOREIGN PATENT DOCUMENTS

| DE | 41 24 338 A | 1/1993 |
| EP | 0 171 268 A2 | 8/1985 |
| EP | 0 236 104 A2 | 9/1987 |
| EP | 0 335 669 | 10/1989 |
| EP | 0 371 736 A2 | 6/1990 |
| EP | 0 541 391 A1 | 5/1993 |
| GB | 1 417 962 A | 12/1975 |
| GB | 2 253 628 A | 9/1992 |
| WO | WO 92/13576 | 8/1992 |

* cited by examiner

Primary Examiner—John M. Cooney, Jr.
(74) Attorney, Agent, or Firm—Woodcock Washburn LLP

(57) ABSTRACT

The invention provides a method of forming a polyurethane foam suitable for use as a wound-contacting layer, said method comprising: mixing 1 part by weight of an isocyanate-capped prepolymer having from 0.5 to 4.8 meq. NCO groups/g with from 0.4 to 1.0 parts by weight of water and an effective amount of a nonvolatile pharmaceutically acceptable acid to form a prepolymer mixture; allowing said prepolymer mixture to cure to form a foamed product; followed by drying the foamed product. The invention also provides acidified polyurethane foams obtainable by this method, and wound dressings comprising such foams.

20 Claims, 1 Drawing Sheet

POLYURETHANE FOAMS FOR USE IN WOUND DRESSINGS

CROSS REFERENCE TO RELATED APPLICATIONS

This application is the U.S. National Phase filing of Application Ser. No. PCT/GB00/00418, filed Feb. 10, 2000, which claims priority to United Kingdom Patent Application Ser. No. 9903097.5, filed Feb. 11, 1999.

This invention relates to polyurethane foams, and more particularly to a method of making conformable, high-density polyurethane foams for use in wound dressings. The invention also relates to a wound dressing having a wound-contacting layer formed from such a foam.

Polyurethane foams have been proposed for a number of uses in the prior art. For example, U.S. Pat. No. 3,903,232 discloses hydrophilic cross-linked polyurethane foams which are said to be useful for external body cleaning, for internal body usage and as absorptive products such as diapers. The foams are prepared by reacting particular isocyanate-capped polyoxyethylene polyols having an isocyanate functionality greater than 2 with large amounts of an aqueous reactant, preferably water.

EP-A-0171268 discloses a dressing for use in deep wounds, which dressing comprises individual pieces of absorbent hydrophilic foam contained within a porous bag formed from an apertured polymeric film. The absorbent foam is preferably a hydrophilic polyurethane foam which can be made from HYPOL (Registered Trade Mark) isocyanate-capped polyether prepolymer marketed by W.R. Grace & Co., and non-ionic surfactants.

According to EP-A-0171268, the fact that the foam is present in the form of individual pieces confers on the dressing the property of being able to conform to the contours of a wound cavity both on initial application of the dressing and subsequently following absorption of body fluids. It is said that existing commercially available foams, if used as a single piece, have too high a density to possess the required degree of conformability.

U.S. Pat. No. 4,339,550 discloses a hydrophilic foam composition which is prepared by the "in situ" reaction of an isocyanate-capped polyether prepolymer having a functionality of from about 2 to about 8, water, and a chemically compatible, essentially non-polar, volatile organic compound. The foam is stated to be capable of achieving a sustained, controlled release of the volatile materials from the foamed structure. Suitable "control release" ingredients include polyols, such as propylene glycol and glycerine.

EP-A-0335669 discloses a hydrophilic foam composition comprising the "in situ" reaction product of an isocyanate-capped polyether prepolymer, a hydrophilic agent capable of absorbing water, an adjuvant comprising an alcohol, a wetting agent and water. One application which is proposed for the foam composition is in the manufacture of wound dressings. The composition is said to carry the adjuvant releasably, so that at least a portion of the adjuvant is released into an external liquid (e.g. wound exudate) with which the foam composition comes into contact.

A wide range of prepolymer, hydrophilic agents, adjuvants and wetting agents are proposed in EP-0335669. Suitable prepolymers are said to include prepolymers having an NCO content as high as 2.55 meq/g or as low as 0.5 to 0.9 meq/g. Water soluble monohydric, dihydric and polyhydric alcohols are all said to be suitable adjuvants, but glycerol is preferred, and the majority of the examples involve the use of glycerol. The sole example in which a monohydric alcohol is employed as the adjuvant involves the use of a prepolymer having an NCO content of 1.6 meq/g. The resulting product is said not to be acceptable because of "gross porosity".

EP-A-0541391 describes a method of forming a polyurethane foam suitable for use as a wound-contacting layer, the method comprising mixing 1 part by weight of an isocyanate-capped prepolymer having from 0.5 to 1.2 meq NCO groups/g with from 0.4 to 1.0 parts by weight of water in the presence of from 0.05 to 0.4 parts by weight of a $C_1$ to $C_3$ monohydric alcohol, and then drying the product such that the amount of water-soluble alcohol remaining in the product is less than 1% by weight. The resulting foam has high density and conformability.

GB-A-1417962 discloses a non-reticulated polyurethane foam material, the foam cells adjacent to at least one surface of which are irreversibly partially collapsed relative to foam cells remote from said surface. The specification notes that polyurethane foam can be reversibly deformed or compressed to reduce the thickness up to a certain extent, but the original thickness will be recovered upon washing or steam heating. In contrast, the "irreversibly partially collapsed" cells are formed by applying a greater degree of compression, but not so great a degree of compression as to cause the cells to collapse completely or fuse.

According to GB-A-2253628, the foams disclosed in GB-A-1417962 are suitable for the treatment of moderately exuding wounds, but they may not have sufficient absorbency to absorb all the exudate from heavily exuding wounds. GB-A-2253628 further reports that an attempt to increase the absorbency of the known foam by incorporating an alginate during manufacture of the foam was unsuccessful. The alginate was said to be degraded, with consequent impairment of its absorbent and haemostatic properties. A deterioration in the appearance of the foam was also noted. However, GB-A-2253628 teaches that alginate may be used to enhance the absorbency of a polyurethane foam, after the foam has already been formed. Thus, the specification discloses a polyurethane foam which is impregnated with alginate, for example by spreading an alginate gel onto the surface of the foam, or immersing the foam in a solution of alginate.

In contrast to the teaching of GB-A-2253628, we have found that alginates can advantageously be incorporated during the production of polyurethane foams, if the foam is formed by mixing an isocyanate-capped prepolymer with a relatively small amount of water. Although the addition of alginate does not substantially increase the absorbency of the polyurethane foam (as measured on a weight per weight basis), it has been found that polyurethane foams containing alginate generally have smaller, more uniform cells, and higher densities.

Accordingly, the present invention provides a method of forming a polyurethane foam suitable for use as a wound-contacting layer, the method comprising mixing one part by weight of an isocyanate-capped prepolymer having from 0.5 to 4.8 meq NCO groups/g with from 0.4 to 1.0 parts by weight of water, characterised in that the mixture further contains from 0.2 to 20% by weight of alginic acid or a salt thereof. Preferably, the alginic acid or alginate salt is present in an amount of from 0.5 to 10% by weight, more preferably 0.5 to 5% by weight, e.g. from 0.75 to 2.5% by weight.

In particularly preferred embodiments, the isocyanate-capped prepolymer has from 0.5 to 1.2 meq. NCO groups/g.

Preferably, the step of mixing is carried out in the presence of from 0.05 to 0.4 parts by weight of a $C_1$ to $C_3$ monohydric alcohol. Subsequent drying of the foam preferably results in a product containing less than 1% by weight of the monohydric alcohol.

The use of a relatively small amount of water in accordance with the present invention produces an initial reaction mixture of relatively high initial viscosity. Carbon dioxide formed by hydrolysis of isocyanate end groups is therefore trapped, producing a foamed hydrogel.

The present invention also provides a polyurethane foam which is suitable for use as a wound-contacting layer, the foam having a density of at least 0.28 g/cm$^3$, and containing from 0.2 to 20% by weight of alginic acid or a pharmaceutically acceptable salt thereof, generally uniformly distributed throughout said foam.

Foams produced according to the method of the invention preferably have a density of at least 0.3 g/cm$^3$. Particularly preferred foams have a density in the range 0.3 to 1.0 g/cm$^3$, e.g. about 0.5 g/cm$^3$.

The foams of the invention also preferably have an elongation at break of at least 150%, and more preferably at least 300%. Particularly preferred foams according to the invention have an elongation at break in the range from 500 to 2000%.

Depending on the proportions of other additives, the foams of the invention have an absorbency of at least 3 g saline/g, preferably at least 5 g/g, and more preferably from 8 to 20 g/g. The foams are thus highly absorbent, yet conformable.

The foams of the invention also have the property of swelling and expanding when water is absorbed. This is particularly advantageous in a wound contact layer, because the swelling of the foam causes it to move inwards towards the wound bed thus filling the wound cavity. This encourages the wound to heal from the base upwards and outwards, and it discourages epithelialization over the wound surface before the bed has been filled with granulation tissue.

The degree of swelling of the foams of the present invention on complete saturation with an aqueous medium is typically at least 100% (expressed in terms of increase in volume), and preferably at least 200%. Preferred foams swell by 400 to 800%. Despite this high degree of swelling, however the foams of the invention retain their integrity even after absorption of large quantities of water.

Moreover, the foams are found to have a morphology which is particularly appropriate for low adherence wound dressings. The foams are open-celled, the cells being very regular in size and shape, with very smooth edges to the pores in the walls of the cells. Typically, the cells of the foams of the invention have an average diameter in the range 0.1 to 0.6 mm.

The prepolymer which is used in the method of the invention is preferably an isocyanate-capped polyether, such as an ethyleneoxy/propyleneoxy copolymer. A particularly suitable prepolymer is that available under Trade Mark HYPOL Hydrogel.

Although the preferred methods of the invention comprehend the use of any of methanol, ethanol or propanol, the use of methanol is particularly preferred. All three alcohols reduce the rate of reaction between the isocyanate-capped prepolymer and water, but the effect of methanol is more marked. A reduction of the reaction rate is desirable in order to facilitate mixing of the various components and spreading of the reaction mixture into a layer of suitable thickness for curing. In addition, the monohydric alcohol serves to end cap some of the NCO end groups, preventing reaction with water to form the urea linkage. This also gives a more flexible, conformable foam.

More preferably, one part by weight of the isocyanate-capped prepolymer is mixed with water in the presence of from 0.05 to 0.25 parts by weight of methanol or from 0.1 to 0.3 parts by weight of ethanol.

It will be appreciated that other components may be added to the reaction mixture in the method of the invention, in order to give desired properties to the product. In particular, it is preferable to include a small proportion (e.g. up to 30% by weight of the wet composition) of a rubber, which may be either natural or synthetic. This has the effect of increasing the cure time for the polyurethane, and increases extensibility, strength and tack.

Most importantly, it substantially reduces shrinkage of the gel on drying, and it also improves bubble formation, producing more regular, smaller bubbles.

Preferably, the rubber is added in the form of a latex, ie. a suspension or emulsion of the rubber in an aqueous medium. The latex will generally comprise 40 to 70% solids by weight, e.g. 50 to 60% by weight. If the foam is to be used as a wound contact layer, the rubber must of course be pharmaceutically acceptable.

Acrylic-based rubbers are particularly preferred. These are commercially available in the form of latexes, such as PRIMAL B-15J and RHOPLEX N-560 (Registered Trade Marks), manufactured by the Rohm & Haas company.

In addition to the methanol or ethanol other alcohols, and particularly polyols, may be included in the reaction mixture to produce a softer, more conformable foam. For example, a polyol sold by Bayer AG under the Registered Trade Mark Levagel may be used. However, traces of such alcohols are likely to remain in the free form after the foaming reaction, and these traces may be difficult to remove from the foam merely by heating. The use of higher boiling alcohols is therefore preferably avoided if the foam is to be used as a wound contact layer, because of the likelihood that such alcohols will be leached from the foam during use of the dressing. When used as or in wound dressings, the foams of the invention contain less than 1% by weight of water soluble alcohols, and more preferably less than 0.1% by weight. It is particularly preferred that the foams of the invention are essentially free of water soluble alcohols (e.g. less that 0.01% by weight).

For use as a wound-contact layer, the foams of the invention may also include topical medicaments and antiseptics, such as silver sulfadiazine, povidone iodine, chlorhexidine acetate and chlorhexidine gluconate, as well as other therapeutically useful additives such as polypeptide growth factors and enzymes.

The present invention also provides a wound dressing comprising a wound contact layer formed from a polyurethane foam as described above, in conjunction with a water-repellant or water-impermeable backing layer. It is greatly preferred that the backing layer also be moisture vapour permeable, as well as being extensible and conformable. A particularly suitable material is a high density polyurethane foam, such as MEDFIX 4003 or 4005 (Registered Trade Mark). These are polyurethane foams of a blocked toluene diisocyanate nature, and are predominantly closed cell.

A particularly advantageous presentation for the dressing of the invention is as an island of wound-contact material on a backing layer, wherein at least the marginal portions of the backing layer are coated with adhesive. Any medically accepted, skin friendly adhesive is suitable, including acrylic, hydrocolloid, polyurethane and silicone based adhesives.

The adhesive may be applied either continuously or discontinuously over the marginal portions of the backing layer. Preferably, however, the adhesive is applied continuously over the whole of the backing layer if the backing layer is not itself impermeable to bacteria, so as to ensure that the backing layer/adhesive combination is impermeable to bacteria It is also preferred that the combination of adhesive and backing layer have a minimum moisture vapour permeability of 400 g/m²/24 hrs, and preferably at least 700 g/m²/24 hrs.

The preferred adhesive is a polyurethane gel material known as LEVAGEL (Registered Trade Mark) and marketed by Bayer AG. This adhesive is made up of three components, namely a modified diphenylmethane diisocyanate, high molecular weight polyhydroxy polyether and a catalyst (dibutyltindilaurate). These three components may be mixed such that the gel contains 4–10 parts (preferably 4.6–6.4 parts) of the modified diphenylmethane diisocyanate, 99.9–99.9975 parts, (preferably 99.94–99.995 parts) of the polyhydroxy polyether and 0.0025–0.1 parts (preferably 0.005–0.06 parts) of the catalyst.

The gel may be mixed by the methods given in U.S. Pat. No. 4,661,099 and applied by conventional coating methods to the backing. The thickness of the gel layer may be between 0.01 mm and 1.0 mm, and preferably between 0.05 mm and 0.5 mm, giving a coating weight of between 25 g/m² and 250 g/m².

The dressing may also contain a wicking layer between the wound contact layer and the backing layer. Such a wicking layer provides absorbency, but more importantly it encourages moisture to move from the wound facing side of the dressing to the back of the dressing where it escapes out of the dressing through the breathable backing. It should have good wicking properties so that moisture can be spread over as large a surface area as possible, thus increasing evaporation The overall effect of this layer is to draw moisture from the wound facing layer, thus decreasing the chances of wound maceration, and to increase evaporation through the backing of the dressing The wicking layer may be formed of several plies (which may or may not be the same) if desired, but it is preferred that the total thickness of the wicking layer does not exceed 1 mm. It is also preferred that the wicking layer be substantially the same size and shape as the wound-facing layer, or slightly smaller than the wound-facing layer.

Suitable materials for the wicking layer include nonwoven, woven and knitted fabrics. Nonwoven viscose fabrics such as those conventionally used for making nonwoven surgical swabs are preferred, but it will be understood that many alternative fabrics particularly other cellulosic fabrics) could be used in their place.

The dressings of the invention will generally be sterile and enclosed in a conventional bacteria-proof envelope. Sterilization may conventionally be carried out using γ-irradiation, but other sterilization methods such as electron beam sterilization may also be used.

The effect of addition of a nonvolatile acid on experimental curing rates of polyurethane foams for use in wound dressings is shown by the following specific embodiments, which are non-limiting examples for the purpose of illustration only.

EXAMPLE 1 (COMPARATIVE)

Methanol (6 g) was added to HYPOL (Registered Trade Mark) Hydrogel prepolymer (50 g; NCO content 0.5–1.2 meq/g) in a disposable cup and mixed thoroughly for a few seconds. Water (32 g) and Latex (12 g) were then added to the HYPOL mixture and stirred vigorously. The foaming mixture was poured onto release paper and spread using a stainless steel hand spreader set at a gap of 2.2 mm. The foam was left to cure and the foam sheet and release paper were placed in an oven (80° C.–100° C.) for 30 min to drive off the water. After cooling, the foam, was lifted from the release paper, allowed to shrink, and replaced on the same paper. The foam was then kiss-cut to size and shape.

EXAMPLES 2–12

The procedure of Example 1 was repeated, but with the addition of varying amounts of sodium alginate and calcium alginate, as set out in the following Table. The Table also shows the absorbency of the foams produced, as determined by the following method:

A sample of foam (approximately 3 g) is prepared and weighed, then placed in a pre-weighed cylindrical wire mesh basket (5 cm diameter, 9 cm depth; 9 cm mesh size). The basket is formed from galvanised steel wire (approx. 0.95 mm thickness), and is closed at one end. The basket and sample are then completely submerged in 0.9% saline solution for 1 hour. The basket is removed from the saline solution, and allowed to drain for 15 seconds, with the closed end down. The basket is then weighed in order to determine the weight of the saturated sample.

| Example | Sodium alginate | Calcium alginate | Absorbency (g/g) |
| --- | --- | --- | --- |
| 1 | — | — | 11.4 |
| 2 | 0.5% | — | 16.1 |
| 3 | 1.0% | — | 15.5 |
| 4 | 2.5% | — | 16.4 |
| 5 | 5.0% | — | 14.6 |
| 6 | 10.0% | — | 14.1 |
| 7 | — | 1.0% | 14.0 |
| 8 | — | 5.0% | 13.4 |
| 9 | — | 10.0% | 12.8 |
| 10 | 0.2% | 0.8% | 14.0 |
| 11 | 1.0% | 4.0% | 13.4 |
| 12 | 2.0% | 8.0% | 13.1 |

It will be seen that the addition of comparatively small amounts of sodium or calcium alginate results in a modest increase in absorbency (on a weight per weight basis), but absorbency decreases with greater quantities of alginate. More importantly, however, the addition of alginate gives rise to smaller and more uniform pores in the foam. This can be seen in the accompanying figures which are scanning electron micrographs at ×20 magnification.

BRIEF DESCRIPTION OF DRAWINGS

FIG. 1 shows a section through a foam according to Example 1, while

Figure 1:
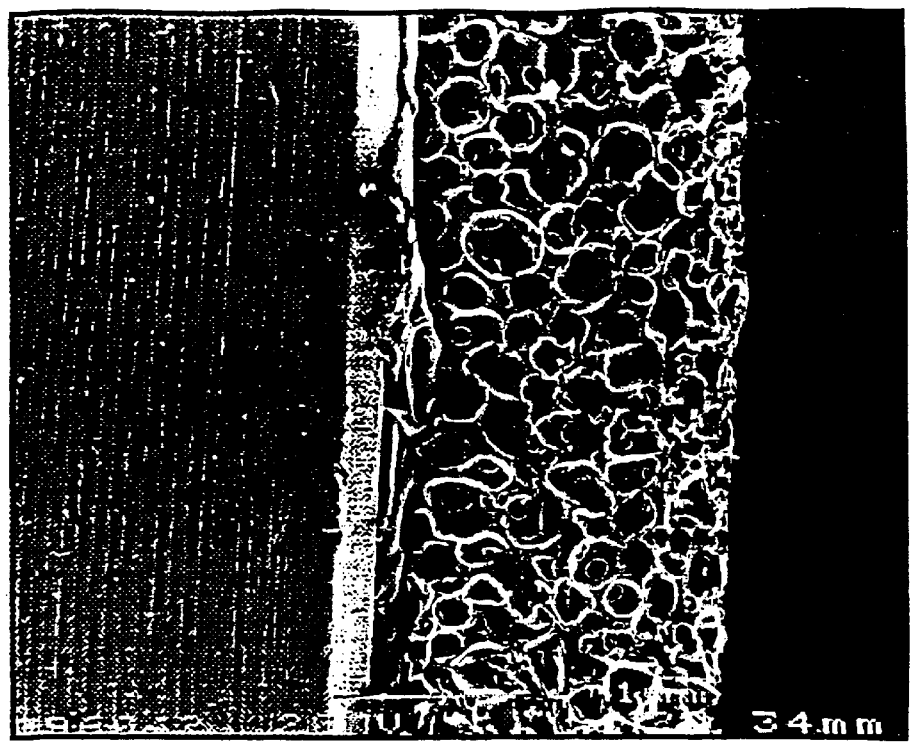
Figure 2:
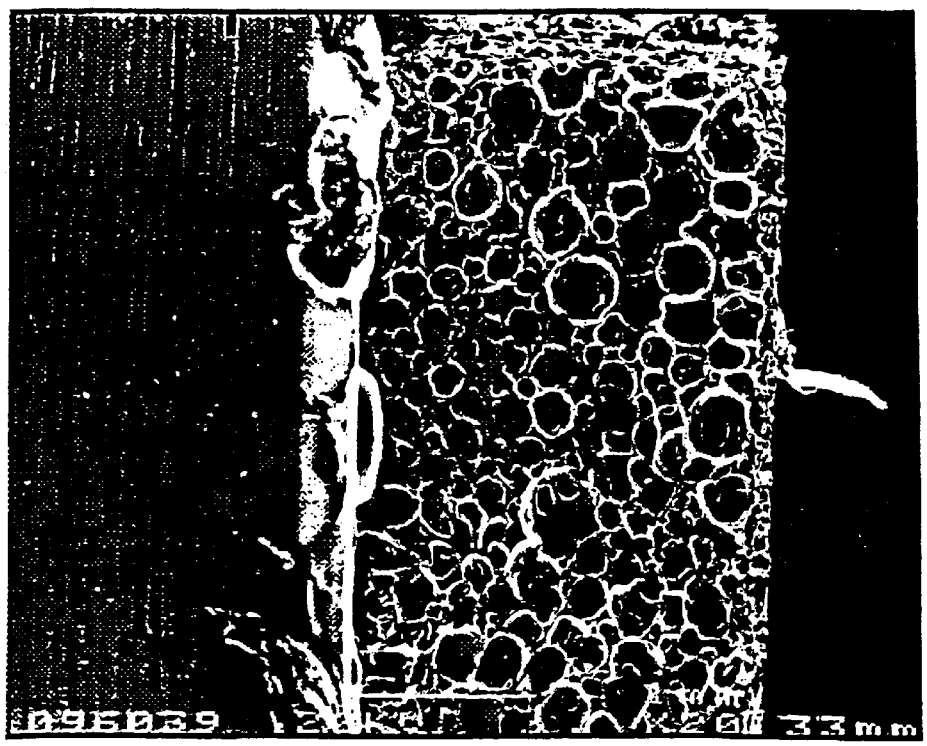
FIG. 2 shows a corresponding section through a foam according to Example 3.

The greater uniformity of pore size has a number of benefits. In particular, the foams of the present invention are more consistent in their absorbency, tensile strength, density and appearance, and they have a reduced tendency to display manufacturing faults such as spreading lines. Moreover, the smaller pore size also means that the foams are of greater density. This, in turn, means that absorbency (on a weight per volume basis) is more substantially increased.

The above embodiments have been described by way of example only. Many other embodiments of the present invention falling within the scope of the accompanying claims will be apparent to the skilled reader.

What is claimed is:

1. A method of forming a polyurethane foam suitable for use as a wound-contacting layer, said method comprising mixing one part by weight of an isocyanate-capped prepolymer having from 0.5 to 4.8 meq NCO groups/gram with from 0.4 to 1.0 parts by weight of water, wherein said mixture further contains from 0.2 to 20% by weight of alginic acid or a salt thereof.

2. A method according to claim 1, wherein the isocyanate-capped prepolymer has from 0.5 to 1.2 meq NCO groups/gram.

3. A method according to claim 1, wherein the step of mixing is carried out in the presence of from 0.05 to 0.4 parts by weight of a $C_1$ to $C_3$ monohydric alcohol.

4. A method according to claim 3, wherein the monohydric alcohol is methanol.

5. A method according to claim 1, wherein the alginic acid salt is sodium alginate, calcium alginate, or a combination thereof.

6. A method according to claim 1, wherein said prepolymer mixture contains from 0.5 to 10% by weight of said alginic acid or salt thereof.

7. A method according to claim 1, wherein said isocyanate-capped prepolymer is an isocyanate-capped polyether prepolymer.

8. A method according to claim 7, wherein said isocyanate-capped polyether prepolymer is an isocyanate-capped ethyleneoxy/propyleneoxy copolymer.

9. A method according to claim 1 wherein one part by weight of the isocyanate-capped prepolymer is mixed with from 0.6 to 0.9 parts by weight water.

10. A method according to claim 3 wherein one part by weight of the isocyanate-capped prepolymer is mixed with water in the presence of from 0.05 to 0.25 parts by weight of methanol or from 0.1 to 0.3 parts by weight ethanol.

11. A polyurethane foam which is suitable for use as a wound-contacting layer, said foam having a density of at least 0.28 grams/centimeter$^3$, and containing from 0.2 to 20% by weight of alginic acid or a pharmaceutically acceptable salt thereof, generally uniformly distributed throughout said foam.

12. A polyurethane foam according to claim 11, wherein said foam contains from 0.5 to 10% by weight of said alginic acid or salt thereof.

13. A polyurethane foam according to claim 11 having a density in the range of from 0.32 to 0.48 grams/centimeter$^3$.

14. A polyurethane foam according to claim 11 having an elongation at break of at least 150%.

15. A polyurethane foam according to claim 14 having an elongation at break of from 500 to 2000%.

16. A polyurethane foam according to claim 11 having an absorbency of at least 10 grams saline/gram.

17. A polyurethane foam according to claim 11 having a swellability on absorption of water of at least 200% by volume.

18. A polyurethane foam according to claim 11, containing less than 0.01% by weight of water-soluble alcohols.

19. A polyurethane foam according to claim 11, wherein said alginic acid salt is sodium alginate, calcium alginate, or a combination thereof.

20. A wound dressing having a wound-contact layer formed from a polyurethane foam according to any one of claims 1 to 19.

* * * * *

UNITED STATES PATENT AND TRADEMARK OFFICE
CERTIFICATE OF CORRECTION

PATENT NO. : 6,509,388 B1  
DATED : January 21, 2003  
INVENTOR(S) : Deborah Addison It is certified that error appears in the above-identified patent and that said Letters Patent is hereby corrected as shown below:

<u>Title page,</u>  
Item [75], Inventor, before "Lancaster (GB)" insert -- Via --;

<u>Column 3,</u>  
Line 24, delete "foam" and insert -- foams --;  
Line 25, delete "s";

<u>Column 4,</u>  
Line 57, delete "MEDFIX" and insert -- MEDIFIX --;

<u>Column 6,</u>  
Line 20, delete second occurrence "9" and insert -- 1 --.

Signed and Sealed this

Seventh Day of September, 2004

JON W. DUDAS  
*Director of the United States Patent and Trademark Office*